US005591208A

United States Patent [19]

Knutson

[11] Patent Number: 5,591,208

[45] Date of Patent: Jan. 7, 1997

[54] EXERCISING FRAME

[76] Inventor: Jeffery N. Knutson, 7915 N. Country Loop, Prineville, Oreg. 97754

[21] Appl. No.: 429,956

[22] Filed: Apr. 27, 1995

[51] Int. Cl.[6] ........................ A61F 5/00

[52] U.S. Cl. ........................ 606/241; 601/24

[58] Field of Search ........................ 5/632, 634, 635, 5/640, 633, 81.1; 297/DIG. 10; 606/241; 601/24

[56] References Cited

U.S. PATENT DOCUMENTS

| | | | |
|---|---|---|---|
| 4,435,863 | 3/1984 | Lerich | 5/81.1 |
| 4,456,086 | 6/1984 | Wier et al. | 297/DIG. 10 |
| 4,623,194 | 11/1986 | Pillot | 297/DIG. 10 |
| 4,802,542 | 2/1989 | Houston . | |
| 4,809,804 | 3/1989 | Houston . | |
| 4,938,533 | 7/1990 | Thielois . | |
| 4,987,622 | 1/1991 | Shockey | 5/81.1 |
| 5,011,224 | 4/1991 | Paul . | |
| 5,054,852 | 10/1991 | Tholkes . | |
| 5,165,753 | 11/1992 | Henderson . | |
| 5,172,925 | 12/1992 | Kendrick . | |
| 5,242,180 | 9/1993 | Bergeron . | |
| 5,265,689 | 11/1993 | Kauffmann . | |
| 5,265,935 | 11/1993 | Geisler et al. . | |
| 5,294,179 | 3/1994 | Rudes et al. . | |

*Primary Examiner*—Lynne A. Reichard
*Attorney, Agent, or Firm*—Michael B. Jolly

[57] ABSTRACT

An exercise frame for use by individuals with limited lower body muscle control utilizing a support frame having fore and aft ends a support member for receiving an extensible means attached to said fore end three upright support members attached to either side of said frame a seat frame work pivotally attached to said upright members, leg, hip, and chest pads attached to said fore end extensible means.

7 Claims, 6 Drawing Sheets

FIG. 7
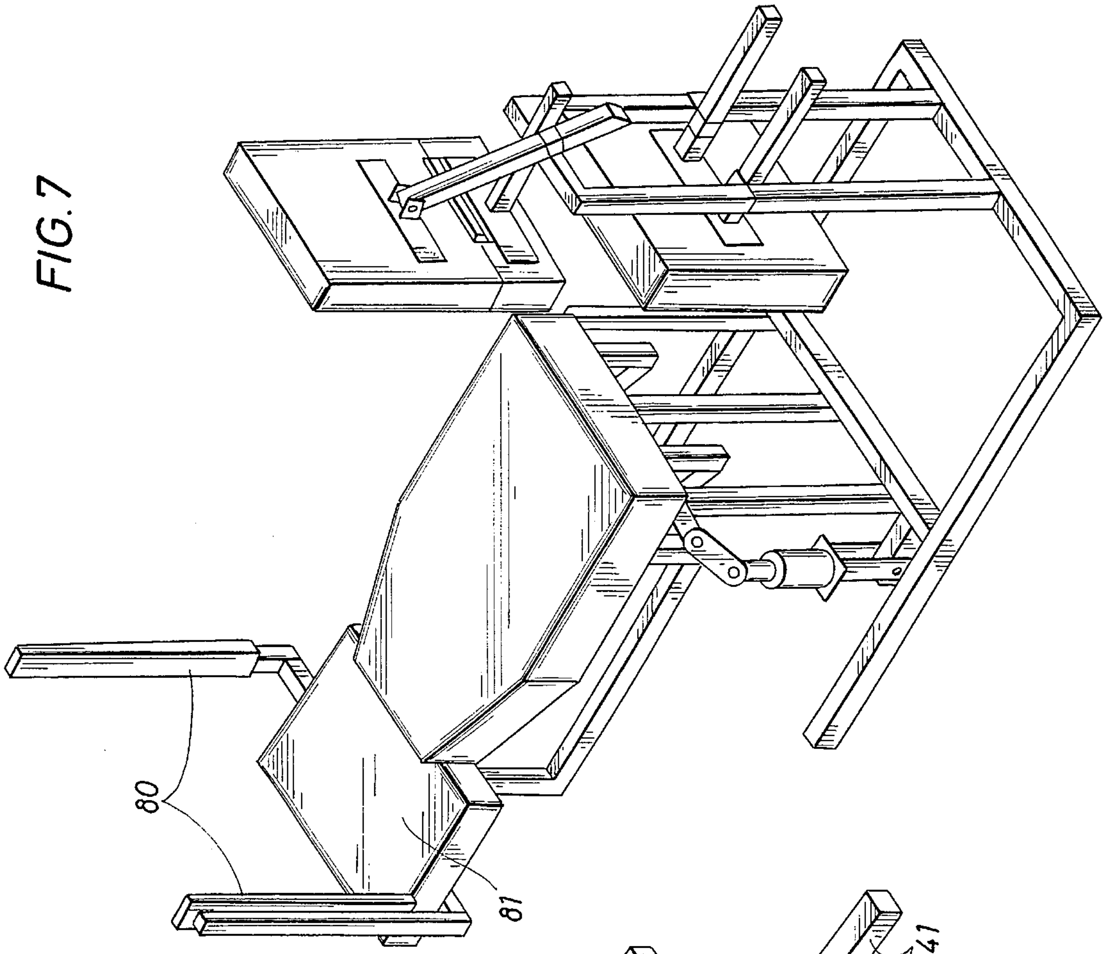
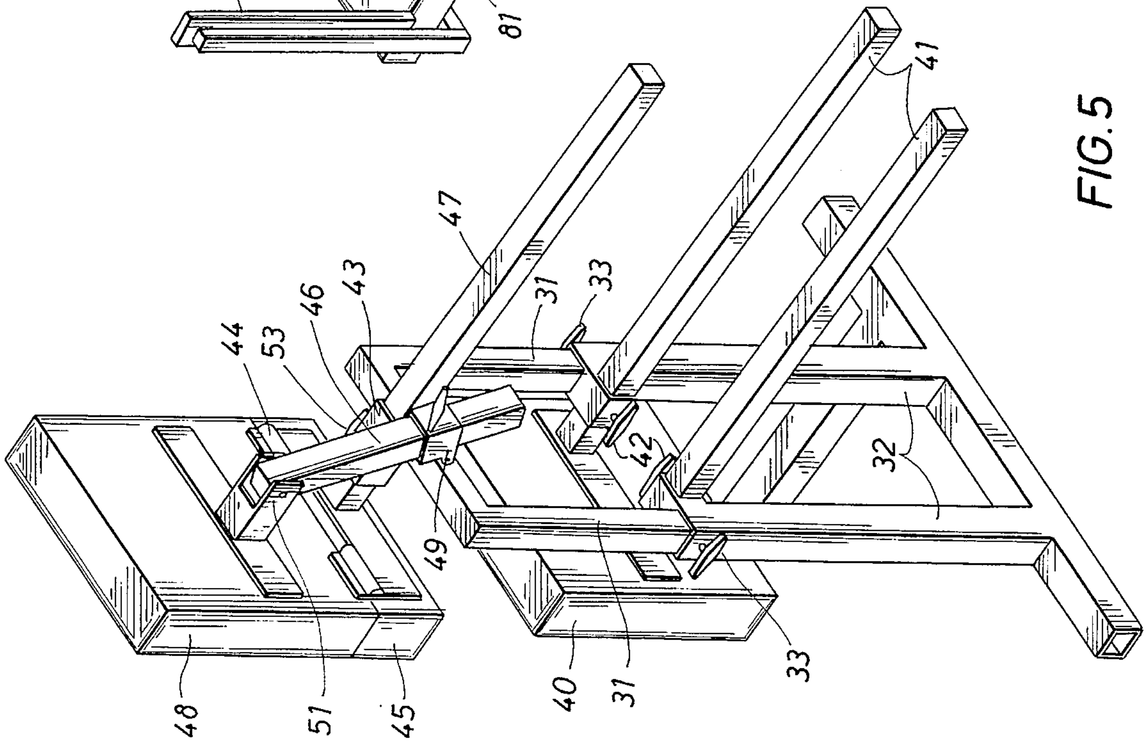
FIG. 5

EXERCISING FRAME

BACKGROUND OF THE INVENTION

This invention relates to an exercising frame for use by paraplegics as a stable support to both raise the user to an upright standing position and to support the user while exercising in the standing position. The frame utilizes a high strength base supporting a manually operated hydraulic one piece seating platform, and manually adjustable leg, hip and chest pads.

Paraplegics and other individuals having limited lower trunk or leg control functions experience progressive atrophy to the lower body muscle groups. These individuals also suffer from bone decalcification, urinary calculi, decreased muscle tone, decreased range of motion, decreased bladder pressure, decreased orthostatic circulatory maintenance, depression and other psychological and physiological complications. It is known that standing has substantial physiological and psychological benefits for these individuals. These individuals have also benefited greatly from exercising while standing.

Standing frames and walkers have been developed which allow the user to both stand and conduct various activities while standing. HOUSTON, U.S. Pat. No. 4,809,804 discloses a combination wheelchair and walker apparatus, HOUSTON, U.S. Pat. No. 4,802,542 discloses a powered walker and THOLKES, U.S. Pat. No. 5,054,852 discloses a utility station with controlled seating. These devises, although useful for raising the user to the standing position are not suitable for the user who also exercises while standing. These devices experience frame flex between the seating platform and the front leg pads when the user conducts front to back bending. Additionally, these devices suffer stability problems when the user conducts side trunk bending. Individuals suffering from sever atrophy of the abdominal and back muscles must rely exclusively upon the structural integrity of the standing frame for support while exercising. Seating supports and front leg, hip, and chest supports must provide sufficient support to enable the user to confidently conduct trunk movements in all directions. Accordingly, there remains a need for an exercise frame which stands the user while also providing a frame with sufficient strength having minimal flex when the user conducts torso bending exercises and further remains stable while the user conducts these exercises.

SUMMARY OF THE INVENTION

It is accordingly an object of the present invention to provide an exercise support frame for individuals with limited or no lower body muscle control permitting the user to exercise while standing.

It is a further object of the invention to provide a manually operated exercise support frame which both raises the user to a standing position and supports the user while exercising in the standing position.

It is another object of the present invention to provide an easily accessible high strength standing frame which remains stable while the user conducts torso movement exercises.

It is another object of the present invention to provide an exercise frame for use by individuals with limited or no lower body muscle control.

It is another object of the present invention to provide an exercise support frame for use by individuals with limited or no lower body muscle control and to provide a means for these individuals to exercise their back, abdominal, oblique and other muscles associated with trunk movement.

It is another object of the present invention to provide an exercise support frame with manually adjustable leg, hip and chest pads so that the frame can be used by individuals of varying size.

It is another object of the present invention to provide an exercise standing frame which has sufficient lateral stability so that the frame remains stable while the user conducts side trunk movement exercises.

It is another object of the present invention to provide an exercise standing frame with a high strength seating platform, high strength leg, hip, and chest pad supports which minimize flex between the platform and the supports while the user is in the standing position conducting front to back bending exercises.

BRIEF DESCRIPTION OF THE DRAWINGS

FIG. 5 is the exercising frame leg, hip, and chest pads,

FIG. 7 is the exercise frame with additional neck and torso support.

DETAILED DESCRIPTION OF THE DRAWINGS

While the present invention will be described fully hereinafter with reference to the accompanying drawings, in which a particular embodiment is shown, it is to be understood at the outset that persons skilled in the art may modify the invention herein described while still achieving the desired result of the invention. Accordingly, the description which follows is to be understood as a broad informative disclosure directed to persons of skill in the appropriate arts and not as limitations upon the present invention.

Figure 1:
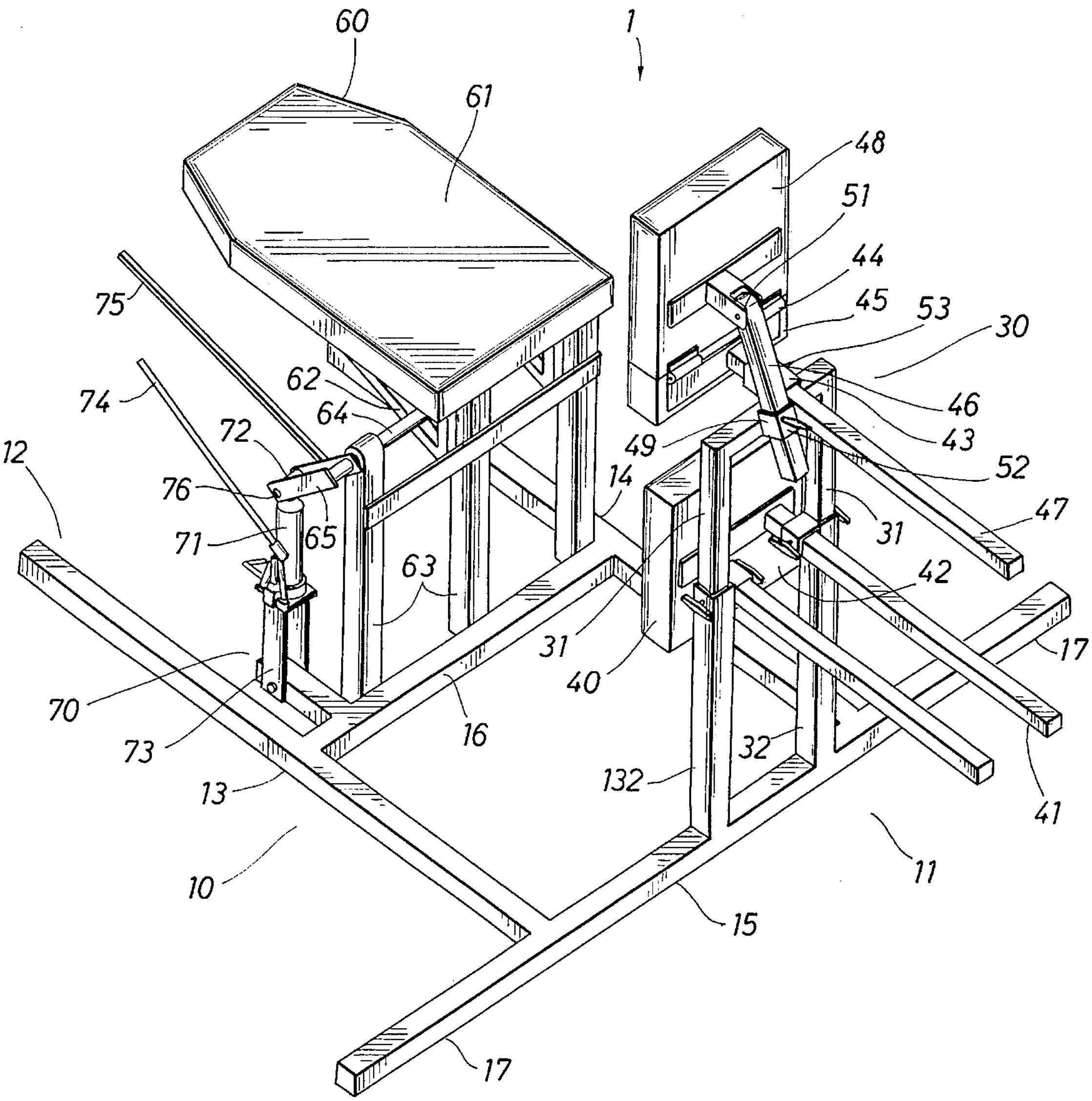
FIG. 1 is the exercising frame in the reclined position.
Figure 2:
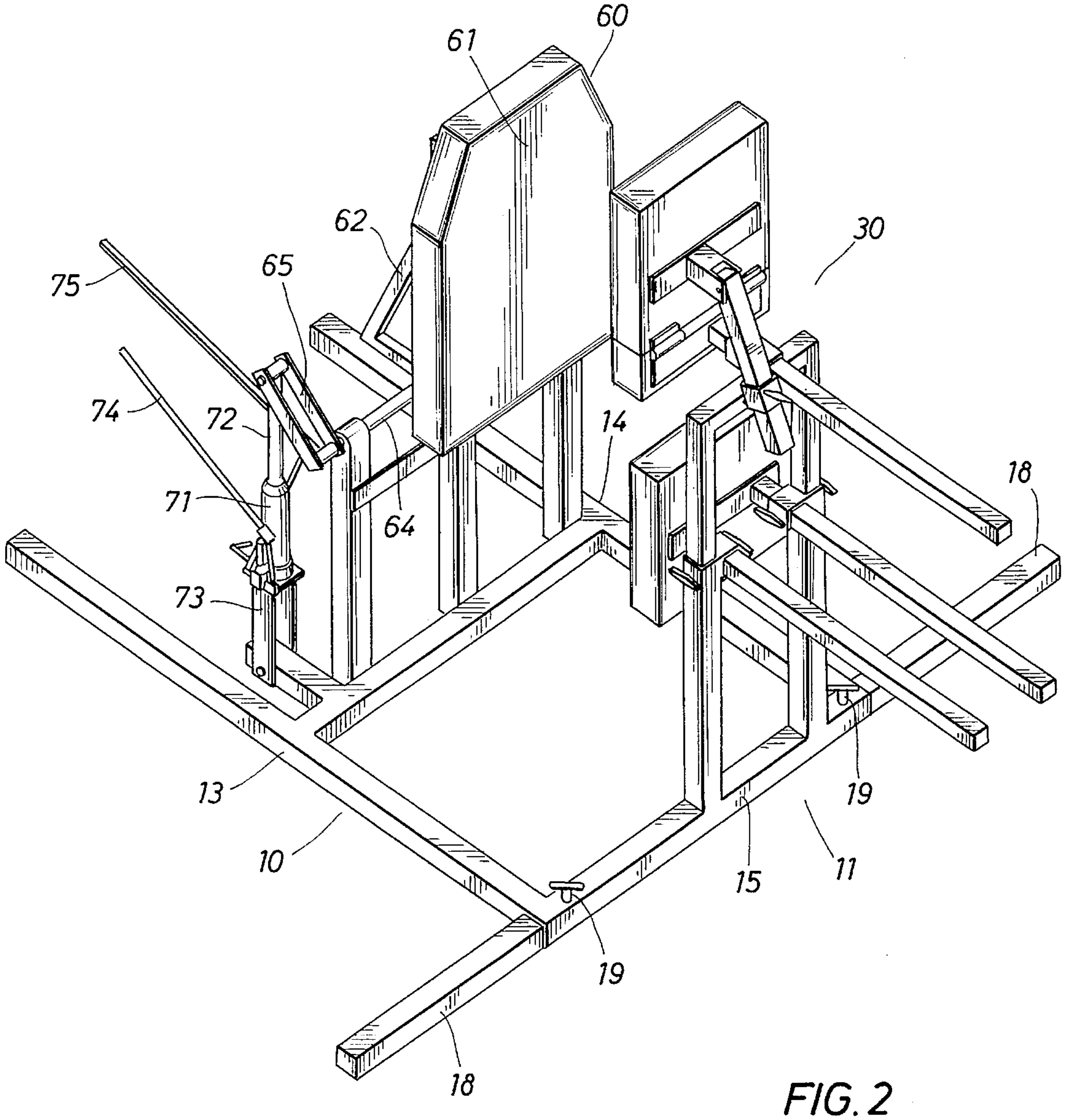
FIG. 2 is the exercising frame in the raised position.
Figure 3:
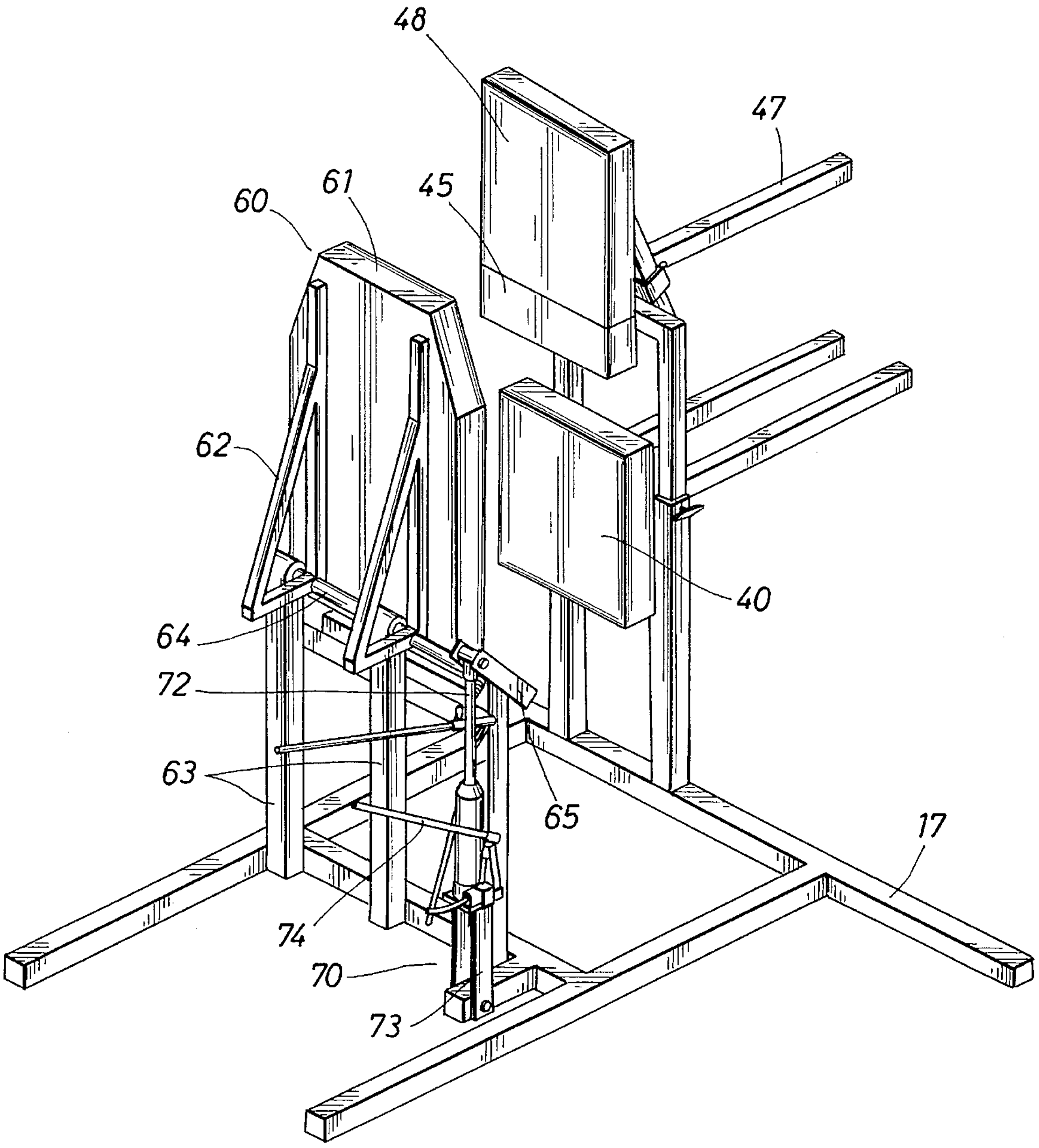
FIG. 3 is a back view of the exercising frame.
Figure 4:
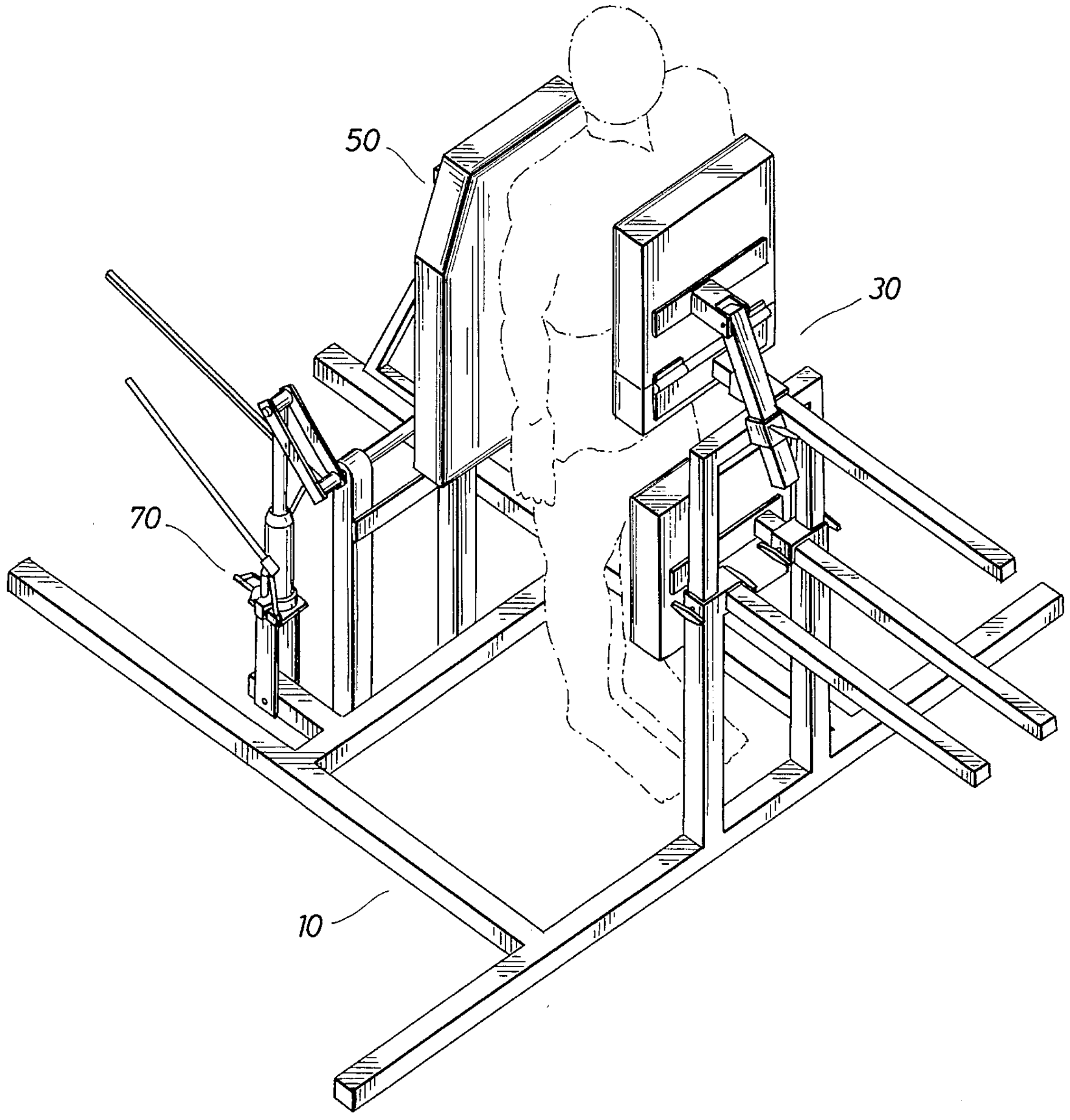
FIG. 4 is the exercising frame with a user in the standing position.
Figure 6:
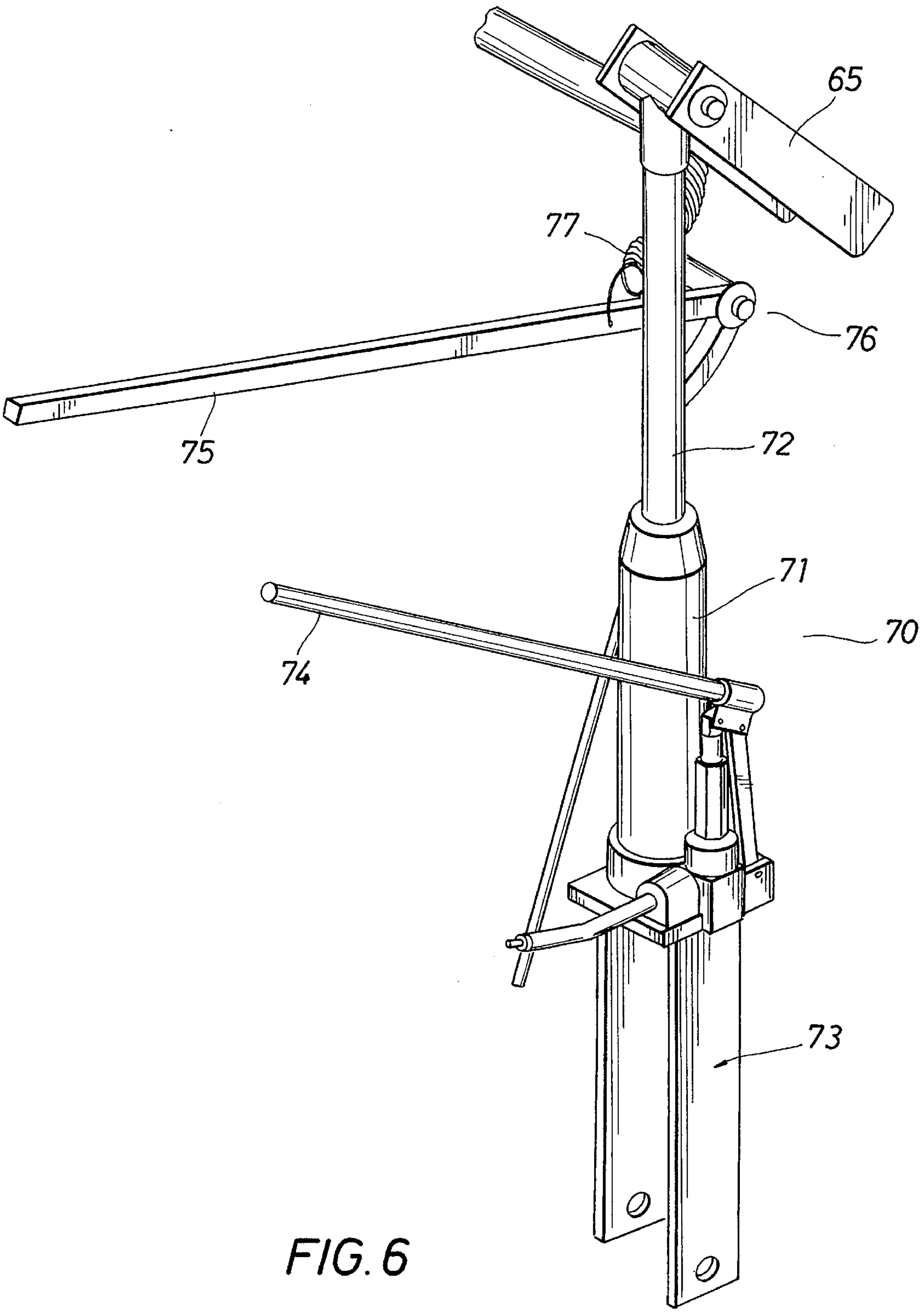
FIG. 6 is the exercise frame hydraulic operating assemble.

FIGS. 1, 2, and 3 illustrate the exercise frame in the lying, standing and rear view standing position respectively, while FIG. 4 illustrates the exercise frame with a user in the standing position. FIGS. 5 and 6 are detailed views of the front leg, hip, and chest pads, and the hydraulic seat raising assemble. FIG. 7 illustrates the frame equipped with additional neck and torso supports. The apparatus will be further described herein with reference to these figures. The exercising frame apparatus 1 is composed of a base frame 10, front leg, hip, and chest support member 30, pivotally mounted one piece seating platform 60, and manual operated hydraulic seat raising assembly 70. The leg, hip, chest and seat pads are most preferable constructed of a rigid padding support, such as wood, plywood, or plastic which is cut to the shape of the given pad, high density foam padding is also cut to the shape of the given pad, the pads are covered with a water proof durable cover such as vinyl.

The apparatus base support frame 10 having fore end 11 and aft end 12 is formed from a pair of longitudinal frame members 13 and 14 which are coupled together using a pair of cross members; one fore cross member 15 attached to the fore end of the longitudinal frame members and another cross member 16 attached mid way between the fore and aft ends of the base. The fore end cross member 15 as illustrated in FIGS. 1, 3, and 4 is constructed of one piece tubing with lateral extending portions 17 extending beyond the longitudinal members. The lateral extension portions 17, for the best mode of operation should extend between twelve inches and twenty four inches beyond the longitudinal members. FIG. 2 illustrates a fore cross member with adjustable lateral extenders 18 with securing means 19. The adjustable lateral extensor 18 are dimensioned to be internally received by fore cross member 15, while the lateral support extensor securing means 19 comprising a pair of threaded shafts extending through apertures on either end of the fore cross member and which frictionally secures the lateral support extensors in place by rotating the threaded shafts. The adjustable lateral extensor 18 allow the user to retract the lateral supports internally into the fore cross member or to extend the extensors if additional lateral support is needed. The frame members are most preferable constructed of round or square tubing from one and one half inches to two inches in diameter. If the lateral extensors are utilized they must be dimensioned to be received internally within the fore end cross member with minimal clearance between the lateral extensor external surface and the fore cross member internal surface.

The hip 45, and chest pads 48 are mounted to a pair of upright extensors 31 which extensors are internally received by a pair of fore end upright supports 32. The fore end upright supports 32 are fixedly attached to fore end cross member 15 and further allow the hip and chest pads to be raised and lowered by the user and adjusted for different user body dimensions. The upright extensors are secured in the desired position by frictional means, and as FIG. 5 indicates a pair of threaded screws 33 extending through the fore end upright supports and further frictionally contacting the extensors 31. The leg pad 40 is supported by a mounting assembly and a pair of extendable supports 41. The leg pad extendable supports are received by a section of framing material fixedly secured to the upright supports and positioned to receive the leg pad extensors perpendicularly to said upright supports. The leg pad extendable supports are secured by a frictional securing means such as that described for the upright extensors. The leg pad is further positioned to be extended toward the chins and knees of the user and accordingly the leg pad is most preferable cuboidal in shape the leg pad functions best when dimensioned so that it contacts both the chins, knees, and upper legs, of the user. Most preferable the leg pad should be between twelve and sixteen inches tall, between ten and fourteen inches wide, and between two and four inches deep. When the user is seated on the exercising frame, the user faces the upright supports and places the front part of her legs next to the leg pads. The legs pads extensors are then extended so that the leg pad firmly contacts the front of the users legs, the extensors are then secured in place. The hip 45 and chest 48 pads are hingedly secured to each other and each is additionally secured to extendable supports. The entire hip, chest pad assemble is height adjustable as per the users desire by use of the upright extensor supports and frictional securing means. The extendable supports for the hip and chest pads are also adjustable as per the user's desire by extending or retracting the extensors and securing them in place by use of frictional securing means. The chest pad extendable support 46 is received by a pivotally mounted receiving member 49. The pivotally mounted receiving member also carries frictional securing means 52 which has been described herein. The hip pad extensor support 47 is received by member 43 which is fixedly secured to upright support 31, receiving member 43 also carries frictional securing means 53. The hip and chest pad receiving members are most preferably dimensioned so that the extensor supports slide easily through the receiving members when the frictional securing means is released. The hip pad is most preferable cuboidal in shape and between ten and twelve inches wide, two to four inches tall and two to four inches deep, while the chest pad is also cuboidal is shape and between ten and twelve inches wide and tall and two to four inches deep. As mentioned above the hip and chest pads are hingedly attached to each by the use of a hinge 44 which is secured on the pad support side and along the top edge of the hip pad and the bottom edge of the chest pad. The hinged pads can be adjusted independently by adjusting the hip or chest pad extensor, in such case the pads' angle relation will change, the pads can also be adjusted in unison which will maintain the pads' angle relationship with one another. The hip pad is most preferable positioned firmly against the user's hip area so that when the user is in the standing position the user's hips are firmly secured between the seat pad and the hip pad. The chest pad adjustment should vary depending on the particular user's abilities. A user with sever atrophy of the trunk and leg muscles should start out with the chest pad adjusted very close to the user's chest or almost parallel with the hip pad, so that the user makes limited forward bending motions. As the user's muscles become more toned the chest pads may be adjusted downwardly or towards a perpendicular position with reference to the hip pad so that the user may make more drastic forward bending motions and thus exercise the torso muscles.

The pivotally mounted one piece seating platform 60 comprises a seat pad 61 and seat pad framework 62, pivot rod 64, and pivot arm 65. The seat pad framework and rod 64 are pivotally mounted on the top end of three upright supports 63, said supports being fixedly attached and perpendicular to cross member 16. The seat framework is most preferably a pair of right triangular frames pivotally secured to the upright supports. The upright supports 63 should be long enough so that the user's legs extend to the ground, most preferable the three upright supports should be between fifteen and eighteen inches high. Pivot arm 65 is fixedly attached to one end of the pivot rod 64 so that when the seat framework is pivoted the pivot arm also pivots. The seat is raised or lowered by use of a hydraulic jack connected to the pivot arm. The manually operated hydraulic seat raising assemble comprises a hydraulic jack 71, hydraulic jack support framework 73, hydraulic ram 72, hydraulic jack handle 74, and hydraulic release lever 75. The hydraulic assemble is pivotally mounted to the base framework by additional frame members 73. The hydraulic support framework is pivotally mounted to the base framework so that the hydraulic assemble may pivot freely as the hydraulic ram is extended or withdrawn so that the seat raising assemble does not bind-up when its' position is changed. The hydraulic jack support framework is further dimensioned to receive the hydraulic jack and provide a means to secure the jack to the support platform, such as screws or bolts. The hydraulic ram 72 is also pivotally connected to the pivot arm by use of a bolt or retaining pin 76, which allows the pivot arm and hydraulic ram connection to pivot as the ram is raised or lowered. The hydraulic jack is manually operated by use of the jack handle 74, which extends the ram 72, which in turn pushes the pivot arm 65 and thus pivots the seating platform, the hydraulic ram is lowered by use of the hydraulic jack release lever 75 such lever being to the closed position by spring 77. The best way to use the seating platform is to place the user on the platform with the hydraulic ram in the lowest position, which will position the seating platform in the longitudinal or lying position, the user does not lie down, but instead supports himself before the seating platform is raised. After securing the user's legs by adjustment of the leg pad, and positioning the hip and chest pads the user then pivots the seating platform by pumping the jack handle and extending the hydraulic ram. As the seating platform is pivoted the seating platform goes from a horizontal position to a vertical position. As the platform makes this movement to the vertical position the user's weight will be transferred to his legs and trunk. When the platform is in the vertical position the user's lower body should be secured between the leg, hip and seating platform, in this position and while the user conducts torso movements the frame, seating platform and hip, chest, and leg assemble are subjected to the most forces which would cause frame flex between the seating platform and the other pads. The use of the three upright supports on this frame prevents a large amount of the flex which is experienced in other exercising frames. The hydraulic release lever 75 is used to release the hydraulic pressure in the hydraulic jack and thus lower the seating platform. The release lever is further biased towards closure by use of tension spring 77, this prevents the seating platform from inadvertently lowering if the release lever slips from the grip of the user.

FIG. 7 illustrates additional supports 81 which help support the user's head and neck if the user has sever atrophy of the neck muscles while the lateral torso supports 80 help the user maintain himself within the frame while conducting side trunck bends.

I claim:

1. An exercise frame for use by individuals with limited or no lower body muscle control, comprising:

a) a support framework having two sides a fore and aft end including a plurality of frame members coupled together to form a base, b) first upright stationary support members secured to said fore end, c) fore end extendable support means received within said first stationary support member, d) second, third, and forth stationary support members secured to said aft end mounted adjacent one another with said second and fourth upright supports mounted on each side of said support framework and said third upright support mounted between said second and forth upright supports, e) a knee pad projecting from said first upright support member and coupled to at least one extensible support arm and a means for securing said knee pad extensible support arm, f) a hip pad having a top edge said hip pad projecting from said fore end extensible support means and coupled to at least one extensible support arm and a means for securing said hip pad extensible support arm, g) a chest pad with a bottom edge and projecting from said fore end extensible support means and pivotally coupled to at least one extensible support arm and a means for pivotally securing said chest pad extensible support arm, further said hip and chest pads are hingedly secured to one another along the hip pad top edge and chest pad bottom edge, h) a hydraulic pump means pivotally secured to said framework adjacent either said second or third upright supports including a hand pump lever and hydraulic pressure release means, i) a seat support framework including a first member pivotally mounted between said second and forth upright support members and a second member pivotally mounted between said third and forth upright support members, means for pivotally coupling said piston to said first and second members, a seat pad secured to said first and second members.

2. Apparatus as set forth in claim 1 including adjustable lateral support members extending transversely from the frame longitudinal members including a means for securing said lateral support members.

3. Apparatus as set forth in claim 1 including a neck support pad and neck pad framework extending beyond said seat pad and further mounted to said seat framework by securing means.

4. Apparatus as set forth in claim 1 including upper body lateral supporting means.

5. Apparatus as set forth in claim 1 including two upper torso stabilizing padded bars fixedly secured to said seat framework and extending transversely from said seat pad surface.

6. Apparatus as set forth in claim 1 wherein said seat framework includes additional support members extending perpendicular said first and second members and additionally cross support extending from one end of said support members, to one end of said addition support members forming a triangular frame pivotally attached to said second, third and forth upright members.

7. Apparatus as set forth in claim 6 including a means for preventing rotation of said seat beyond a right angle to said upright support members, including a cross member fixedly secured to said second, third and forth upright support members and positioned so that when the seat framework rotates downwardly to a right angle to the upright supports the seat framework contacts the fixed cross member and prevents further rotation in the downward direction.

* * * * *